United States Patent
Ferritto et al.

(10) Patent No.: US 6,887,934 B2
(45) Date of Patent: May 3, 2005

(54) RESIN MODIFIED ELASTOMERS

(75) Inventors: Michael Salvatore Ferritto, Midland, MI (US); Tina Marie Leaym, Saginaw, MI (US); William James Schulz, Jr., Midland, MI (US); Janet Mary Smith, Swartz Creek, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/227,516

(22) Filed: Aug. 26, 2002

(65) Prior Publication Data

US 2004/0039132 A1 Feb. 26, 2004

(51) Int. Cl.$^7$ .............................................. C08L 83/05
(52) U.S. Cl. ........................... 524/588; 528/12; 528/31; 528/32; 528/39; 528/25; 424/65; 424/70.1; 424/78.02
(58) Field of Search ........................... 524/588; 528/12, 528/31, 32, 39, 25; 424/65, 70.1, 78.02

(56) References Cited

U.S. PATENT DOCUMENTS

| | | | | |
|---|---|---|---|---|
| 4,987,169 A | | 1/1991 | Kuwata et al. ............. 524/267 |
| 5,399,614 A | * | 3/1995 | Lin et al. .................... 524/588 |
| 5,760,116 A | * | 6/1998 | Kilgour et al. ............. 524/268 |
| 5,833,973 A | | 11/1998 | Dobkowski et al. ..... 424/18.08 |
| 5,849,314 A | | 12/1998 | Dobkowski et al. ........ 424/401 |
| 5,919,468 A | | 7/1999 | Bara ........................... 424/401 |
| 5,977,280 A | * | 11/1999 | Kadlec et al. |
| 6,388,005 B1 | * | 5/2002 | Morita et al. |
| 6,423,322 B1 | * | 7/2002 | Fry ............................. 424/401 |

FOREIGN PATENT DOCUMENTS

| | | | |
|---|---|---|---|
| EP | 0 917 870 A1 | 11/1997 | ............ A61K/7/48 |
| EP | 0 852 945 B1 | 12/1997 | ............ A61K/7/48 |
| EP | 0 827 983 | 3/1998 | |
| EP | 0 908 175 A1 | 9/1998 | ............ A61K/7/48 |
| EP | 1 057 476 | 12/2000 | |
| WO | WO 97/44010 | 5/1997 | ............ A61K/7/48 |
| WO | WO 98/00105 | 6/1997 | ............ A61K/7/48 |
| WO | WO 98/35649 | 3/1998 | ............ A61K/7/42 |
| WO | WO 98/42307 | 3/1998 | ............ A61K/7/48 |
| WO | WO 99/43297 | 2/1999 | ............ A61K/7/48 |
| WO | WO 99/51192 | 3/1999 | ............ A61K/7/00 |

* cited by examiner

Primary Examiner—Kuo-Liang Peng
(74) Attorney, Agent, or Firm—Alan Zombeck

(57) ABSTRACT

Resin modified elastomers, methods of making them and their uses. The method for making the elastomers comprises reacting in a diluent an ≡SiH functional siloxane; a diene, diyne or ene-yne compound, a resin having the formula $(R^1{}_3SiO_{1/2})_x(SiO_{4/2})_y(R^1SiO_{3/2})_z$ where each $R^1$ is independently a monovalent hydrocarbon group having 1 to 30 carbon atoms or an unsaturated hydrocarbon group having 2 to 30 carbon atoms x is $\geq 1$, $y \geq 0$, $z \geq 0$ and $y+z \geq 1$.

38 Claims, No Drawings

RESIN MODIFIED ELASTOMERS

FIELD OF THE INVENTION

This invention relates to resin modified elastomers, methods of making them and their uses. The method for making the elastomers comprises reacting in a diluent an ≡SiH functional siloxane; a diene, diyne or ene-yne compound, a resin having the formula $(R^1_3SiO_{1/2})_x(SiO_{4/2})_y(R^1SiO_{3/2})_z$ where each $R^1$ is independently a monovalent hydrocarbon group having 1 to 30 carbon atoms or an unsaturated hydrocarbon group having 2 to 30 carbon atoms x is $\geq 1$, $y \geq 0$, $z \geq 0$ and $y+z \geq 1$.

BACKGROUND OF THE INVENTION

Silicone based materials comprising cross-linked siloxanes dispersed in a diluent are known in the art. One such material, made by polymerization of certain organohydrogenpolysiloxanes along with organopolysiloxanes having aliphatic unsaturated groups while in the presence of certain low viscosity silicones, is disclosed in U.S. Pat. No. 4,987,169 to Kuwata et al. Another such material is disclosed in U.S. Pat. No. 5,760,116 to Kilgour et al. In this last instance, certain alkenyl stopped polyorganosiloxanes are hydrosilylated with ≡SiH containing "MQ" silicone resins in the presence of certain other silicones.

There are of course many variations possible in these materials and the synthesis of such materials. For example, the ≡SiH groups and the aliphatic unsaturation may be on either or even both hydrosilylation reactants, as may other functionality. Sometimes, this allows for the synthesis of the same or a very similar type material using very different reactants in the same type of reaction. For example, what could be called a variant of Kilgour is seen in EP 1 057 476 by Fry, wherein the unsaturation appears in the resin and the ≡SiH functionality appears in the other hydrosilylation reactant.

As with many other silicone based materials, it is has been found that inclusion of certain functional groups in the silicone material can impart or enhance desirable properties. One example, where the polyether functionality is used, can be seen in U.S. Pat. No. 5,811,487 to Schulz et al. Here, the polyether functionality was introduced by hydrosilylation prior to cross-linking. It may also be of note that the cross-linker may be purely hydrocarbon as was the case in this last mentioned material.

The present invention provides resin modified silicone based elastomers capable of suitably enhancing durability of personal care products while providing desirable aesthetics. Because the nature in which the resin functionality is introduced into the elastomer it is possible by the instant invention to produce materials having a variety of aesthetic properties for use in the personal care formulations.

SUMMARY OF THE INVENTION

This invention pertains to resin modified silicone elastomers. The resin modified elastomers comprise:
(A) a cross-linked siloxane comprising:
   a siloxane polymer resin functionality having the formula $(R_3SiO_{1/2})_x(SiO_{4/2})_y(RSiO_{3/2})_z$ and cross-links, -E-Y-E-, with each end of the cross-link is bonded to a silicon atom in the siloxane polymer,
   wherein,
      each R is independently a divalent hydrocarbon group having 2 to 30 carbon atoms or a monovalent hydrocarbon group having 1 to 30 carbon atoms wherein when R is a divalent hydrocarbon group it is bonded to the resin and the siloxane polymer;
      each E is a divalent group independently selected from —CH$_2$CH$_2$— or —CH=CH—;
      Y is a divalent group that is a hydrocarbon, a siloxane or some combination of these;
      x is $\geq 1$, $y \geq 0$, $z \geq 0$ and $y+z \geq 1$.
   and
(B) a diluent.

This invention further pertains to methods of making the resin modified elastomers. One method comprises cross-linking, in the presence of a hydrosilylation catalyst,
   (1) an ≡SiH functional siloxane,
   (2) a diene, diyne or ene-yne compound,
   (3) a resin having the formula $(R^1_3SiO_{1/2})_x(SiO_{4/2})_y(R^1SiO_{3/2})_z$ where each $R^1$ is independently a monovalent hydrocarbon group having 1 to 30 carbon atoms or a unsaturated hydrocarbon group having 2 to 30 carbon atoms, x, y, and z are as defined above; wherein (1), (2) and (3) are dispersed in a diluent, and there is 0.1 to 100 weight parts of diluent per weight part of (1), (2) and (3).

In addition, the invention relates to personal care products containing the compositions of the present invention.

DETAILED DESCRIPTION OF THE INVENTION

This invention pertains to resin modified elastomers. The resin modified elastomers comprise:
A) a cross-linked siloxane comprising:
   a siloxane polymer resin functionality having the formula $(R_3SiO_{1/2})_x(SiO_{4/2})_y(RSiO_{3/2})_z$ and cross-links, -E-Y-E-, with each end of the cross-link is bonded to a silicon atom in the siloxane polymer,
   wherein,
      each R is independently a divalent hydrocarbon group having 2 to 30 carbon atoms or a monovalent hydrocarbon group having 1 to 30 carbon atoms wherein when R is a divalent hydrocarbon group it is bonded to the resin and the siloxane polymer;
      each E is a divalent group independently selected from —CH$_2$CH$_2$— or —CH=CH—;
      Y is a divalent group that is a hydrocarbon, a siloxane or some combination of these;
      and
      x is $\geq 1$, $y \geq 0$, $z \geq 0$ and $y+z \geq 1$;
   and
(B) a diluent.

The siloxane polymer is typically comprised of $R^3_2SiO$ units but may also contain units of the formula $R^3_3SiO_{1/2}$, $R^3SiO_{3/2}$ and $SiO_{4/2}$ where $R^3$ is a monovalent hydrocarbon group, alternatively a monovalent hydrocarbon group having 1 to 30 carbon atoms.

The resin functionality in the cross-linked siloxane may be chemically bonded or blended into the cross-linked siloxane. When the resin functionality is chemically bonded into the cross-linked siloxane at least one R in the resin is a divalent hydrocarbon group having 2 to 30 carbon atoms. R as a divalent hydrocarbon group (R') may be exemplified by, but not limited to, alkylene groups such as ethylene, hexenylene, propylene, and mixtures thereof, preferably ethylene (—CH$_2$CH$_2$—). The remaining R groups are independently monovalent hydrocarbons groups having 1 to 30 carbon atoms, preferably methyl, alternatively phenyl, or alternatively combinations thereof. Typically one of the R groups is ethylene and two are methyl, alternatively one of the R groups is ethylene, one is methyl and one is phenyl.

When the resin functionality is chemically bonded into the cross-linked siloxane it is typically bonded into the backbone of the siloxane polymer but it may be bonded in the cross-links or both the backbone of the siloxane polymer and cross-links. It is possible a particular siloxane molecule may have several different types of backbone elements as well as several different cross-linker elements. The resin functionality can be distributed among these in any fashion as long as present somewhere in the cross-linked siloxane molecule.

When the resin functionality is blended into the cross-linked siloxane all of the R groups are monovalent hydrocarbon groups having 1 to 30 carbon atoms. R as a monovalent hydrocarbon group (R") may be exemplified by, but not limited to, alkyl groups such as methyl, ethyl, isopropyl; phenyl and mixtures thereof, preferably methyl ($CH_3$—).

It is also possible to have the resin both chemically and covalently bonded into the cross-linked siloxane by using a mixture of resins.

The resin functionality is comprised of at least one $R_3SiO_{1/2}$ unit and at least one unit selected from $SiO_{4/2}$ and $RSiO_{3/2}$. The resin functionality may be exemplified by, but not limited to, resins of the formula $(R_3SiO_{1/2})_x(SiO_{4/2})_y$ where x and y have a ratio of from 0.5:1 to 1.5:1 and by resins of the formula $(R_3SiO_{1/2})_x(RSiO_{3/2})_z$.

The amount of resin functionality in the siloxane is from 1 to 30 mole %, alternatively 5 to 20 mole % based on the moles of siloxane units in the siloxane polymer.

The cross-linked siloxane also contain crosslinks of the formula -E-Y-E- where each E is a divalent hydrocarbon group independently selected from —$CH_2CH_2$— or —CH=CH— and Y is a divalent group that is a hydrocarbon, a siloxane or some combination of these. Typically each E is —$CH_2CH_2$— and Y is a hydrocarbon group having 1 to 30 carbon atoms alternatively 1 to 10 carbon atoms. The cross-links may be exemplified by, but not limited to pentylene, hexylene, heptylene, octylene, decylene, dodecylene, tetradecylene and others. When Y is a siloxane it typically has the formula

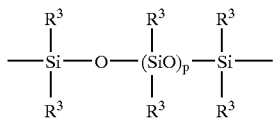

where $R^3$ is a monovalent hydrocarbon group and p is 0 to 20,000, alternatively 0 to 500.

The amount of cross-link functionality in the siloxane is from 1 to 20 mole %, alternatively 3 to 10 mole % based on the moles of siloxane units in the siloxane polymer.

The resin modified elastomers also comprise a diluent (B). Suitable examples include silicones, both linear and cyclic (other than the corresponding cross-linked siloxane (A)), organic oils, organic solvents and mixtures of these. Specific examples of diluents may be found in U.S. Pat. No. 6,200,581, which is hereby incorporated by reference for this purpose. Non-reactive or relatively non-reactive diluents are preferred. For purposes here, non-reactive is used in reference to the associated cross-linking reaction and used relative to the (other) reactants therein. A relatively non-reactive diluent would be less than one tenth as reactive with the other reactants as the others are with each other in the associated cross-linking reaction. The weight ratio range for (A):(B) is typically 1:100 to 10:1, alternatively 1:50 to 2:1, alternatively 1:20 to 1:1.

One embodiment of the resin modified elastomer is where the cross-linked siloxane (A) has the average formula:

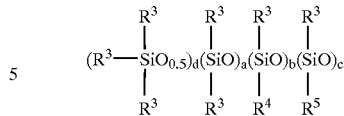

where, $R^3$ is a monovalent hydrocarbon group having 1 to 30 carbon atoms;

$R^4$ is resin functional group having the formula $(R'R''_2SiO_{1/2})_x(SiO_{4/2})_y$ where R', R", x and y are as defined above and where x and y have a ratio of from 0.5:1 to 1.5:1.

$R^5$ is a cross-link -E-Y-E- or a siloxane containing (somewhere in its structure as pendant, internal, terminal or otherwise) -E-Y-E-; where E and Y are as defined above where one end of the cross-link is bonded into the siloxane (I) and the other end of the cross-link is bonded into a unit having the formula ($\equiv SiO_{1/2}$) wherein the remaining two bond sites on the Si in this unit are selected from oxygen, $R^3$, $R^4$, $R^5$ or any combination thereof; and a is 0 to 100,000,000 (alternatively 100 to 10,000,000);
b is 1 to 50,000,000 (alternatively 1 to 5,000,000);
c is 1 to 10,000,000 (alternatively 1,000,000); and
$4 \leq d \leq 2c+2$.

In the above formula (I) $R^3$ is preferably a monovalent hydrocarbon group having 1 to 30 carbons, alternatively 1 to 18 carbons and in particular alkyl, aryl, alkaryl, aralkyl, or combinations thereof. Alternatively $R^3$ is methyl. Y is preferably a divalent hydrocarbon group having 1 to 30 carbon atoms.

Another embodiment of the resin modified elastomer is where the cross-linked siloxane (A) has the average formula:

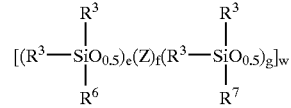

where, $R^3$ is a monovalent hydrocarbon group having 1 to 30 carbon atoms;

each $R^6$ is independently a monovalent hydrocarbon group or $R^4$ wherein $R^4$ is as defined above with the proviso that at least one $R^6$ group is $R^4$;

$R^7$ is a cross-link having the formula -E-$R^8$—Y—$R^9$-E-, or a siloxane containing a cross-link having the formula -E-$R^8$—Y—$R^9$-E-; where E and Y are as defined above and one end of the cross-link is bonded into the siloxane (II) and the other end of the cross-link is bonded to a unit having the formula ($\equiv SiO_{1/2}$) wherein the remaining two bond sites on the Si in this unit are selected from oxygen, $R^3$, $R^4$, $R^7$ or any combination thereof;

Z is on average at least 80 mole percent ($SiO_2$) with the balance made up of one or more other types of siloxane units;

$R^8$ and $R^9$ are independently divalent hydrocarbon groups or nullities;

w is 1 to 100 (alternatively 1 to 70);
e is 1 to 500 (alternatively 2 to 300);
f is 1 to 1,000 (alternatively 1 to 500); and
g is 1 to 100 (alternatively 1 to 50);

with the proviso that the ratio of e+f: g is 0.5 to 4.0 (alternatively 0.6 to 3.5).

In the above siloxane (II), $R^3$ and $R^6$ are typically monovalent hydrocarbon groups having 1 to 30, alternatively 1 to 20 carbons. $R^8$ and $R^9$ are typically divalent hydrocarbon groups having 1 to 8 carbons. Y is preferably a divalent hydrocarbon group having 1 to 30 carbon atoms.

It should be understood that in this disclosure and the claims that follow that "siloxane units" refers to one of the silicon based building blocks found in siloxanes and polysiloxanes. These are commonly referred to in the art as "M" ($\equiv SiO_{1/2}$), "D" ($=SiO$), "T" ($—SiO_{3/2}$) and "Q" ($SiO_2$) units, as well as functionalized and/or substituted versions of these. One particular "T" type siloxane unit of interest in siloxane (II) is "T-OH" ($HO—SiO_{3/2}$).

In the context of a divalent R or similarly designated divalent group, it should be understood that "nullity" means "nothing there". For example, in -E-$R^8$—Y—$R^9$-E-, if —$R^8$— is a nullity, then -E-$R^8$—Y—$R^9$-E- is the same as -E-Y—$R^9$-E-.

Another embodiment of the resin modified elastomer is where the cross-linked siloxane (A) has subunits of the formula:

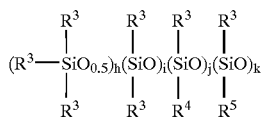

(III)

where,
$R^3$, $R^4$, and $R^5$ are as described above;
i is 0 to 1,000;
j is 1 to 500;
k is 1 to 100; and
$4 \leq h \leq 2k+2$.

Another embodiment of the resin modified elastomer is where the cross-linked siloxane (A) has subunits of the formula

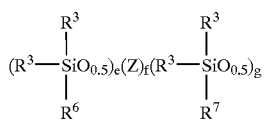

(IV)

where $R^3$, $R^6$, $R^7$, Z, and e, f, and g are as described above.

The present invention also relates to methods of making the resin modified elastomers. One method comprises reacting, in the presence of a hydrosilylation catalyst, (1) an $\equiv SiH$ functional siloxane,
(2) a diene, diyne or ene-yne compound,
(3) a resin having the formula $(R^1_3SiO_{1/2})_x(SiO_{4/2})_y$ $(R^1SiO_{3/2})_z$ where $R^1$, x, y and z are as defined above;

wherein (1), (2) and (3) are dispersed in a diluent (B), and there is 0.1 to 100 weight parts of diluent per weight part of (1), (2) and (3).

Any hydrosilylation catalyst, of which many are well known in the art, may be utilized, such as those based on noble metals like platinum, notably Karstedt's catalyst. Karstedt's catalyst, a platinum divinyl tetramethyl disiloxane based composition, is described extensively in the art such as in U.S. Pat. No. 5,654,362. Homogeneous, heterogeneous or mixtures of homogeneous and heterogeneous form catalysts may be employed. The hydrosilylation catalysts are used in amounts from 0.00001 to 0.5 parts per 100 weight parts of the $\equiv SiH$ functional siloxane, alternatively 0.00001 to 0.02 parts, alternatively 0.00001 to 0.002 parts.

It may be advantageous in some instances to control reaction using a catalyst quencher. Quenching of this type is presented in U.S. Pat. No. 5,929,164. It is not essential that a quencher be used in the methods of the present invention, but one may be employed if desired.

In component (1), the $\equiv SiH$ functionality may be pendant, internal, terminal or otherwise or some combination of these. The $\equiv SiH$ functional siloxane includes those comprising at least one unit selected from $R^3HSiO_{2/2}$, $HSiO_{3/2}$ and $R^3_2HSiO_{1/2}$ where $R^3$ is as previously described. Typically the $\equiv SiH$ functional siloxane contains $\geq 2$ of these units, alternatively 2 to 600 of these units.

The $\equiv SiH$ functional siloxane may be exemplified by, but not limited to

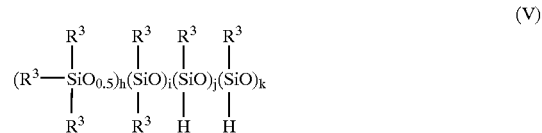

(V)

where $R^3$, h, i, j, and k are as described previously; and more specifically by $[(CH_3)_3SiO_{0.5}]_l[(CH_3)_2HSiO_{0.5}]_m[(CH_3)_2SiO]_n[(CH_3)HSiO]_o$ (VI)

where
l is 0 to 2;
m is 0 to 2;
l+m=2;
n is 0 to 20,000 (alternatively 100 to 5000 or 500 to 5000);
o is 0 to 2000 (alternatively 0 to 200); and
m+o$\geq$2;
and by

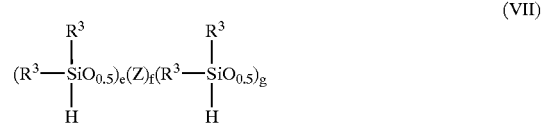

(VII)

where $R^3$, Z, e, f and g are as described above.

Component (2) is a diene, diyne or ene-yne compound. Diene, diyne or ene-yne compounds are those compounds wherein there is at least two aliphatic unsaturated groups with some separation between the groups. Structurally, component (2) can be, in the "alpha, omega diene" case, $HC\equiv C—Y—C\equiv CH$, where Y is a divalent group that is a hydrocarbon, siloxane or some combination of these. The unsaturation could be at an end or pendant if part of a polymer molecule. Component (2) may be exemplified by, but not limited to, $E^1$-Y-$E^1$ where each $E^1$ is independently $CH_2=CH—$ or $CH\equiv C—$ and Y is as defined above; a siloxane containing two $E^1$-Y-E- groups; a siloxane having the formula

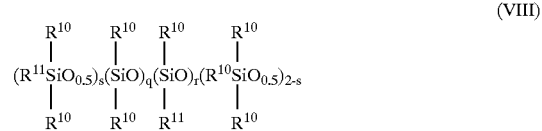

(VIII)

where q is 0 to 20,000 (alternatively 100 to 20,000 or 100 to 5000);
r is 0 to 2000,
s is 0 to 2,
$2 \leq s+r \leq 2000$,
$R^{10}$ is a monovalent hydrocarbon having 1 to 30 carbons and $R^{11}$ is a monovalent, terminally aliphatic unsaturated hydrocarbon having from two to twelve carbons;
and a siloxane having the formula

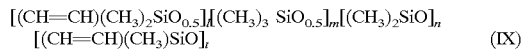

$$[(CH\!=\!CH)(CH_3)_2SiO_{0.5}]_l[(CH_3)_3\,SiO_{0.5}]_m[(CH_3)_2SiO]_n\\ [(CH\!=\!CH)(CH_3)SiO]_t \qquad (IX)$$

where l, m and n are as previously defined and t is 0 to 1000 (alternatively 0 to 50) and l+t≧2. In formula (IX) n is preferably 0 to 500.

Component (2) may be further exemplified by, but not limited to 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne.

Component (3) is a resin having the formula $(R^1_3SiO_{1/2})_x(SiO_{4/2})_y(R^1SiO_{3/2})_z$ where $R^1$, x, y, and z are as defined above. In addition to the $R^1_3SiO_{1/2}$, $SiO_{4/2}$ and $R^1SiO_{3/2}$ units, the resins may contain hydroxyl or alkoxy functional units and even some divalent siloxane units ($R^1_2SiO$), provided however, that these units are present only in small amounts.

$R^1$ may be exemplified by alkyl radicals such as methyl or ethyl; the phenyl radical and alkenyl radicals such as vinyl, allyl and hexenyl. Typically $R^1$ is selected from the group consisting of methyl and vinyl. When it is desirous to chemically bond the resin into the elastomer at least one $R^1$ is an alkenyl group, typically a vinyl group. These resins will contain 0.01 to 22 wt % alkenyl functionality, alternatively 0.6 to 20 wt % alkenyl functionality or 0.6 to 8 wt % alkenyl functionality. When it is desirous to have the resin blended into the elastomer $R^1$ is typically methyl, phenyl or any combination thereof.

One example of resins useful herein have the formula $(R^1_3SiO_{1/2})_x(SiO_{4/2})_y$. The mole ratio of $(R^1_3SiO_{1/2})$ units to $(SiO_{4/2})$ units in this resin has a value of from 0.5:1 to 1.5:1, alternatively 0.6:1 to 1.1:1. These mole ratios are easily measured by 29Si NMR spectroscopy. Typically the presence of silicon-bonded hydroxyl groups (i.e. $HOR^{10}_2SiO_{1/2}$ or $HOSiO_{3/2}$ is kept below 0.7 wt % based on the total weight of the resin, alternatively below 0.3 wt %.

The reaction to produce the resin modified elastomer is carried out in a diluent (B). Suitable diluents include silicones, both linear and cyclic, organic oils, organic solvents and mixtures of these. Specific examples of diluents may be found in U.S. Pat. No. 6,200,581, which is hereby incorporated by reference for this purpose. Non-reactive or relatively non-reactive diluents are preferred.

Specifically, the diluent may be a low viscosity silicone typically having a viscosity in the range of 100 to 1,000 mm²/sec such as hexamethylcyclotrisiloxane, octamethylcyclotetrasiloxane, decamethylcyclopentasiloxane, dodecamethylcyclohexasiloxane, octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, hexamethyl-3,3,bis{(trimethylsilyl)oxy}trisiloxane pentamethyl{(trimethylsilyl)oxy}cyclotrisiloxane as well as polydimethylsiloxanes, polyethylsiloxanes, polymethylethylsiloxanes, polymethylphenylsiloxanes, polydiphenylsiloxanes.

Typically the diluent is a volatile silicone. By volatile it is meant having a boiling point less than about 250° C. and a viscosity of about 0.65 to 5.0 mm²/s.

Organic diluents may be exemplified by, but not limited to, aromatic hydrocarbons, aliphatic hydrocarbons, alcohols, aldehydes, ketones, amines, esters, ethers, glycols, glycol ethers, alkyl halides and aromatic halides.

The amount of diluent is such that there is 0.1 to 100 weight parts of diluent per weight part of (1), (2) and (3), alternatively 0.5 to 50 parts of diluent, alternatively 1 to 20 parts.

The method for producing the resins is not critical. Typically the ≡SiH functional siloxane, resin and diluent and hydrosilylation catalyst are combined and the reaction is carried out to produce a resin-modified ≡SiH functional siloxane. The amount of resin used is typically from 0.1 to 50 mole % resin based on the total moles of SiH in component (1), alternatively 5 to 20 mole %.

Thereafter the diene, diyne or ene-yne compound (2) is added to cross-link the resin modified ≡SiH functional siloxane to produce the resin modified elastomer. Component (2) is used in an amount to provide 0.7 to 1.3 part of unsaturation in (2) per part ≡SiH functionality. Typically (2) is used in an amount to provide 0.8 to 1.1 part of unsaturation in (2) per part ≡SiH. Typically the reaction is carried out with an excess of unsaturation per part ≡SiH.

Alternatively the ≡SiH functional siloxane, resin, diene, diyne or ene-yne compound, diluent and hydrosilylation catalyst are combined and the reaction is carried out to produce the resin modified elastomer.

In any case it is necessary to add the resin to the reaction mixture prior to or during the cross-linking reaction.

Typically the reaction is carried out at a temperature of 40° C. to 100° C., alternatively 65° C. to 95° C.

Another method for producing the resin modified elastomers comprises cross-linking, in the presence of a hydrosilylation catalyst,
(1) a ≡SiH functional siloxane containing $R^4$ groups where $R^4$ is as defined previously, and
(2) a diene, diyne or ene-yne compound,
wherein (1) and (2) are dispersed in a diluent, and there is 0.1 to 100 weight parts of diluent per weight part of (1) and (2). The resin modified elastomers may be prepared by first reacting the ≡SiH functional siloxane with the resin described as component (3) above. Component (2) is used in an amount to provide 0.7 to 1.3 parts unsaturation in (2) per part ≡SiH functionality. Typically (2) is used in an amount to provide 0.8 to 1.1 parts unsaturation in (2) per part ≡SiH functionality.

It is sometimes convenient to express a composition (implicitly) in terms of a method to make it. This invention includes compositions that are the product of (made by, prepared by, etc.) any of the methods of the present invention, as well as any preparable by any of these methods. In corresponding claims, the former would be expressed in "product by process" terms, while the latter would be expressed in broader terms ("preparable by") which is broader than "the product of", "made by", "prepared by" or other language of that type. A "preparable by" claim would cover a composition that could be made by the cited method, even if it actually was not.

The resin modified elastomers of the present invention are often clear and nearly solid materials. These may be diluted with a suitable diluent ("second diluent") to form pastes, gels or fluids as required. The second diluent may selected from the diluents described above that are used in the preparation of the resin modified elastomer. Typically the second diluent is added in an amount of 1% to 50% based on weight solids in the resin modified elastomer.

The resin modified elastomers may be thermodynamically stable. By thermodynamically stable it is meant a material comprising a cross-linked polymer and a diluent that is homogeneous immediately after shearing and remains as such for at least 72 hours after being sheared, where homogeneous refers to something with a constant bulk viscosity (the type measured in units of cP, mPa s or equivalent units such as in a Brookfield device and sometimes referred to as absolute viscosity as opposed to kinematic viscosity) throughout a given sample within +/- 10 percent at any given point in time.

One method for determining such thermodynamic stability is wherein a sample of material is first sheared then visually inspected for homogeneity. If the sheared material is found to be visually homogenous, then viscosity is measured using a statistically significant number of random samples of the sheared material taken immediately after the visual inspection and again 72 hours later. The material is considered thermodynamically stable if all viscosity measurements (for accuracy's sake, these are taken as, respectively, the mean of several measurements at the same point) from the initial sampling and the sampling 72 hours later are within +/−10 percent of their respective means.

The invention also includes compositions, such as personal care products, made from any of the compositions of the present invention previously described herein. This would include hair, skin and underarm care products, more specifically conditioners, moisturizers, body washes, cosmetic foundations, blushes, lipsticks, eye liners, mascaras, eye shadows, antiperspirants and deodorants. Other examples of products that can be made using the compositions of the present invention are the same as can be made from the materials disclosed in U.S. Pat. No. 6,200,581, which is hereby incorporated by reference for these examples.

The personal care products contain the resin modified elastomer of the instant invention and at least one personal care product ingredient. Examples of personal care product ingredients include, but are not limited to, ester waxes, oils and fats of animal or vegetable origin, fatty alcohols, fatty acids, alkyl esters of fatty acids; hydrocarbon oils and waxes; water, organic solvents, perfumes, surfactants, oil-soluble vitamins, water-soluble vitamins, oil-soluble drugs, water-soluble drugs, actives, pharmaceutical compounds and others.

It should be understood that in the context of a chemical formula that Me stands for methyl. Further, compositions expressed in percent should be taken as being in weight percent, unless otherwise indicated.

It should be understood that ranges should be interpreted as specifically including and disclosing all sub ranges and individual values subsumed. For example, a range of 1 to 10 would include and disclose a range of 2–5 and a range of 6–8, as well as 1.72, 7.76 and 9.9, among other sub ranges and individual values in the overall range. Of course, this understanding would apply correspondingly to other types of ranges, such as "C1 to C5 hydrocarbons" and "a value of at least 80 percent".

In reference to polymer formulae "average" should be understood to be a number or molar average, unless otherwise indicated. Also, it should be understood that formulae given for polymers (such as the one for the cross linked siloxane given just above) should be regarded as only semi-structural such that the subscripts for various subunits indicate merely the number present in the molecule as opposed to the particular position shown. Further, no stereospecificity is intended by what is shown in such formulae.

Titles in the examples that follow are merely descriptive and should not be viewed as limiting in any way.

The following non-limiting examples are provided so that one skilled in the art may more readily understand the invention.

EXAMPLES

In the following examples by MQ resin it is meant a resin having the general formula $(Me_2VisiO_{1/2})_x(SiO_{4/2})_y$.

Example 1

Into a vessel was added 36.2 g of a MQ resin ($M_n$=2,700, 2.16 weight percent vinyl) and 400 g of decamethylcylcopentasiloxane. The mixture was heated to 70° C. and upon complete dissolution of the resin, 57.8 g of the dimethyl methylhydrogen siloxane copolymer (DP=93, 6.6 mole percent methyl hydrogen groups) was added followed by 10 ppm of platinum catalyst. The mixture was held at 70° C. with mixing for 1 hour. Next, 1.2 g of 1,5-hexadiene was added and the mixture was stirred for an additional 3 hours. Next, additional decamethylcylcopentasiloxane is added to achieve the desired level of solid. The resulting product is a clear thick paste.

Example 2

Into a vessel was added 18.8 g of a MQ resin ($M_n$=2,690, 0.88 weight percent vinyl) and 26.8 g of a second MQ resin (Mn=4,320, 0.96 weight percent vinyl) and 415 g of decamethylcylcopentasiloxane. The mixture was heated to 70° C. and upon complete dissolution of the resin, 38.4 g of a dimethyl methylhydrogen siloxane copolymer (DP=188, 6.5 mole percent methyl hydrogen groups) was added followed by 10 ppm of platinum catalyst. The mixture was held at 70° C. with mixing for 1 hour. Next, 0.9 g of 1,5-hexadiene was added and the mixture was stirred for an additional 3 hours. Next, additional decamethylcylcopentasiloxane is added to achieve the desired level of solids. The resulting product is a thick paste.

Example 3

Into a vessel was added 26.5 g of a MQ resin ($M_n$=4,200, 0.0 weight percent vinyl) and 430 g of decamethylcylcopentasiloxane. The mixture was heated to 70° C. and upon complete dissolution of the resin, 42.0 g of the dimethyl methylhydrogen siloxane copolymer (DP=93, 6.6 mole percent methyl hydrogen groups) was added followed by 10 ppm of platinum catalyst. The mixture was held at 70° C. with mixing for 1 hour. Next, 1.5 g of 1,5-hexadiene was added and the mixture was stirred for an additional 3 hours. Next, additional decamethylcylcopentasiloxane is added to achieve the desired level of solids.

Example 4

Into a vessel was added 33.2 g of a MQ resin ($M_n$=4,180, 2.09 weight percent vinyl) and 430 g of decamethylcylcopentasiloxane. The mixture was heated to 70° C. and upon complete dissolution of the resin, 36.5 g of the dimethyl methylhydrogen siloxane copolymer (DP=93, 6.6 mole percent methyl hydrogen groups) was added followed by 10 ppm of platinum catalyst. The mixture was held at 70° C. with mixing for 1 hour. Next, 0.65 g of 1,5-hexadiene was added and the mixture was stirred for an additional 3 hours. Next, additional decamethylcylcopentasiloxane is added to achieve the desired level of solids.

Example 5

Into a vessel was added 45.4 g of a MQ resin ($M_n$=4,180, 2.09 weight percent vinyl) and 400 g of decamethylcylcopentasiloxane. The mixture was heated to 70° C. and upon complete dissolution of the resin, 53.7 g of a dimethyl methylhydrogen siloxane copolymer (DP=265, 6.0 mole percent methyl hydrogen groups) was added followed by 10 ppm of platinum catalyst. The mixture was held at 70° C. with mixing for 1 hour. Next, 0.9 g of 1,5-hexadiene was added and the mixture was stirred for an additional 3 hours. Next, additional decamethylcylcopentasiloxane is added to achieve the desired level of solids.

Example 6

Into a vessel was added 52.4 g of a MQ resin ($M_n$=2,650, 0.0 weight percent vinyl) and 400 g of decamethylcylcopentasiloxane. The mixture was heated to 70° C. and upon complete dissolution of the resin, 46.1 g of the dimethyl methylhydrogen siloxane copolymer (DP=93, 6.6 mole percent methyl hydrogen groups) was added followed by 10 ppm of platinum catalyst. The mixture was held at 70° C. with mixing for 1 hour. Next, 1.5 g of 1,5-hexadiene was added and the mixture was stirred for an additional 3 hours. Next, additional decamethylcylcopentasiloxane is added to achieve the desired level of solids.

Comparative Example 1

Into a vessel was added 96.6 g of the dimethyl methylhydrogen siloxane copolymer (DP=99, 6.0 mole percent methyl hydrogen groups) and 400 g of decamethylcylcopentasiloxane. The mixture was heated to 70° C. with mixing. To this mixture was added 10 ppm of platinum catalyst. Next, 3.40 g of 1,5-hexadiene was added and the mixture was stirred for an 3 hours. Next, additional decamethylcylcopentasiloxane is added to achieve the desired level of solids.

What is claimed is:

1. A resin modified elastomer comprising:
   (A) a cross-linked siloxane comprising:
      (i) a siloxane polymer,
      (ii) resin functionality having the formula $(R_3SiO_{1/2})_x(SiO_{4/2})_y(RSiO_{3/2})_z$ and
      (iii) cross-links, -E-Y-E-, with each end of the cross-link is bonded to a silicon atom,
   wherein,
      each R is independently a divalent hydrocarbon group having 2 to 30 carbon atoms or a monovalent hydrocarbon group having 1 to 30 carbon atoms; wherein when R is a divalent hydrocarbon group it is bonded to the resin and to the siloxane polymer or a cross-link;
      each E is a divalent group independently selected from —CH$_2$CH$_2$— or —CH═CH—;
      Y is a divalent group that is a hydrocarbon having from 1 to 30 carbon atoms; and
      x is ≧1, y≧0, z≧0 and y+z≧1; and
   (B) a diluent.

2. The resin modified elastomer of claim 1 wherein E is —CH$_2$CH$_2$— and Y is a divalent hydrocarbon group having from 1 to 10 carbon atoms.

3. The resin modified elastomer of claim 1 wherein the resin functionality has the formula $(R_3SiO_{1/2})_x(SiO_{4/2})_y$ where x and y have a ratio of from 0.5:1 to 1.5:1.

4. The resin modified elastomer of claim 1 wherein the resin functionality has the formula and by resins of the formula $(R_3SiO_{1/2})_x(RSiO_{3/2})_z$.

5. The resin modified elastomer of claim 1 wherein the resin functionality is chemically boned into the cross-linked siloxane.

6. The resin modified elastomer of claim 1 wherein the resin functionality is blended into the cross-linked siloxane.

7. The resin modified elastomer of claim 1 wherein the resin functionality is bonded or blended into the cross-linked siloxane.

8. The resin modified elastomer of claim 1 wherein the cross-linked siloxane contains 1 to 30 mole % of resin functionality based on the moles of siloxane units in the siloxane polymer.

9. The resin modified elastomer of claim 1 wherein the cross-link is selected from pentylene, hexylene, heptylene, octylene, decylene, dodecylene and tetradecylene.

10. The resin modified elastomer of claim 1 wherein the cross-linked siloxane contains 1 to 20 mole % cross-link based on the moles of siloxane units in the siloxane polymer.

11. The resin modified elastomer of claim 1 wherein the diluent is selected from silicones, organic solvents or mixtures thereof.

12. The resin modified elastomer of claim 11 wherein the diluent is a cyclic silicone.

13. The resin modified elastomer of claim 11 wherein the diluent is a linear silicone.

14. The resin modified elastomer of claim 1 wherein the cross-linked siloxane and diluent are present in a weight ratio of 1:100 to 10:1.

15. The resin modified elastomer of claim 1 wherein the cross-linked siloxane and diluent are present in a weight ratio of 1:50 to 2:1.

16. The resin modified elastomer of claim 1 wherein the cross-linked siloxane and diluent are present in a weight ratio of 1:20 to 1:1.

17. The resin modified elastomer of claim 1 wherein (A) has the average formula

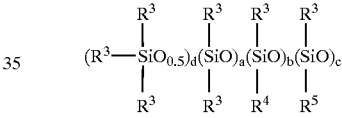

where,
   $R^3$ is a monovalent hydrocarbon group;
   $R^4$ is resin functional group having the formula $(R'R''_2SiO_{1/2})_x(SiO_{4/2})_y$ where R' is a divalent hydrocarbon group having 2 to 30 carbon atoms, each R" is independently a monovalent hydrocarbon group having 1 to 30 carbon atoms and x and y have a ratio of from 0.5:1 to 1.5:1;
   $R^5$ is a cross-link -E-Y-E- or a siloxane containing -E-Y-E-; where one end of the cross link is bonded into the siloxane and the other end of the cross-link is bonded into a unit having the formula (≡SiO$_{1/2}$) wherein the remaining two bond sites on the Si in this unit may be oxygen, $R^3$, $R^4$, $R^5$ or any combination thereof; and
   a is 0 to 100,000,000;
   b is 1 to 50,000,000;
   c is 1 to 10,000,000; and
   4≦d≦2c+2.

18. The resin modified elastomer of claim 17 wherein in (A)
   $R^3$ is a monovalent hydrocarbon group having 1 to 30 carbons,
   $R^5$ is a cross-link —CH$_2$CH$_2$—Y—CH$_2$CH$_2$— where one end of the cross link is bonded into the siloxane and the other end of the cross-link is bonded into a unit having the formula (≡SiO$_{1/2}$) wherein the remaining two bond sites on the Si in this unit may be oxygen, $R^3$, $R^4$, $R^5$ or any combination thereof Y is a divalent hydrocarbon group having from 1 to 30 carbons; and (B) is a silicone other than (A) or a mixture of silicones not containing (A).

19. The resin modified elastomer of claim 1 wherein (A) is a cross-linked siloxane of average formula:

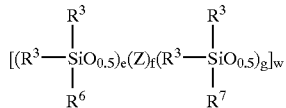

where,

R$^3$ is a monovalent hydrocarbon group;

R$^6$ is a monovalent hydrocarbon group or R$^4$ wherein R$^4$ is resin functional group having the formula (R'R"$_2$SiO$_{1/2}$)$_x$(SiO$_{4/2}$)$_y$ where R' is a divalent hydrocarbon group having 2 to 30 carbon atoms and R" is a monovalent hydrocarbon group having from 1 to 30 carbon atoms, and x and y have a ratio of from 0.5:1 to 1.5:1; with the proviso that at least one R$^6$ group is R$^4$.

R$^7$ is a cross-link having the formula -E-R$^8$—Y—R$^9$-E-, or a siloxane containing a cross-link having the formula -E-R$^8$—Y—R$^9$-E-; wherein each E is a divalent group independently selected from —CH$_2$CH$_2$— or —CH=CH—; Y is a divalent group that is a hydrocarbon, a siloxane or some combination of these; R$^8$ and R$^9$ are independently divalent hydrocarbon groups or nullities and where one end of the cross-link is bonded into the siloxane (A) and the other end of the cross-link is bonded to a unit having the formula (≡SiO$_{1/2}$) wherein the remaining two bond sites on the Si in this unit may be oxygen, R$^3$, R$^4$, R$^7$ or any combination thereof;

Z is on average at least 80 mole percent (SiO$_2$) with the balance made up of one or more other types of siloxane units;

w is 1 to 100;

e is 1 to 500;

f is 1 to 1,000; and g is 1 to 100; with the proviso that e+f: g is 0.5 to 4.0.

20. The resin modified elastomer of claim 19 where in (A) R$^3$ is a monovalent hydrocarbon group having from 1 to 30 carbons;

R$^7$ is -E-R$^8$—Y—R$^9$-E-;

R$^8$ and R$^9$ are independently divalent hydrocarbons groups having from 1 to 8 carbons or a nullity; and Y is a divalent hydrocarbon group having 1 to 30 carbon atoms.

21. The resin modified elastomer of claim 1 wherein:

(A) is a cross-linked siloxane comprising subunits of formula:

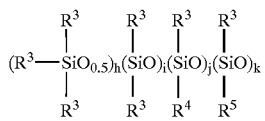

where,

R$^3$ is a monovalent hydrocarbon group;

R$^4$ is resin functional group having the formula (R'R"$_2$SiO$_{1/2}$)$_x$(SiO$_{4/2}$)$_y$ where R' is a divalent hydrocarbon group having 2 to 30 carbon atoms, each R" is a monovalent hydrocarbon group having 1 to 30 carbon atoms and x and y have a ratio of from 0.5:1 to 1.5:1;

R$^5$ is a cross-link -E-Y-E- or a siloxane containing -E-Y-E- where one end of the cross link is bonded into the siloxane and the other end of the cross-link is bonded into a unit having the formula (≡SiO$_{1/2}$) wherein the remaining two bond sites on the Si in this unit may be oxygen, R$^3$, R$^4$, R$^5$ or any combination thereof, i is 0 to 1,000;

j is 1 to 500;

k is 1 to 100; and

4≦h≦2k+2.

22. The resin modified elastomer of claim 1 wherein (A) is a cross-linked siloxane comprising subunits of formula:

(IV)

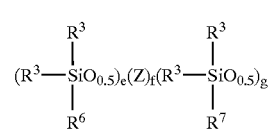

R$^3$ is a monovalent hydrocarbon group;

R$^6$ is a monovalent hydrocarbon group or R$^4$ wherein R$^4$ is resin functional group having the formula (R'R"$_2$SiO$_{1/2}$)$_x$(SiO$_{4/2}$)$_y$ where R' is a divalent hydrocarbon group having 2 to 30 carbons, each R" is a monovalent hydrocarbon group having 1 to 30 carbons, and x and y have a ratio of from 0.5:1 to 1.5:1;

R$^7$ is a cross-link having the formula -E-R$^8$—Y—R$^9$-E-, or a siloxane containing a cross-link having the formula -E-R$^8$—Y—R$^9$-E-; wherein each E is a divalent group independently selected from —CH$_2$CH$_2$— or —CH=CH—; Y is a divalent group that is a hydrocarbon, a siloxane or some combination of these; R$^8$ and R$^9$ are independently divalent hydrocarbon groups or nullities and where one end of the cross-link is bonded into the siloxane (A) and the other end of the cross-link is bonded to a unit having the formula (≡SiO$_{1/2}$) wherein the remaining two bond sites on the Si in this unit may be oxygen, R$^3$, R$^4$, R$^7$ or any combination thereof;

Z is on average at least 80 mole percent (SiO$_2$) with the balance made up of one or more other types of siloxane units;

e is 1 to 500;

f is 1 to 1,000; and g is 1 to 100; with the proviso that e+f: g is 0.5 to 4.0.

23. A composition comprising (1) the resin modified elastomer as claimed in claim 1;

(2) a second diluent.

24. The composition as claimed in claim 23 wherein the second diluent is selected from the group consisting of silicones, organic oils, organic solvents or mixtures thereof.

25. A personal care product comprising (1) the resin modified elastomer as claimed in claim 1 and (2) at least one personal care product ingredient.

26. The personal care product as claimed in claim 25 wherein the personal care product ingredient is selected from ester waxes, oils and fats of animal or vegetable origin, fatty alcohols, fatty acids, alkyl esters of fatty acids; hydrocarbon oils and waxes; water, organic solvents, perfumes, surfactants, oil-soluble vitamins, water-soluble vitamins, oil-soluble drugs, water-soluble drugs, actives, pharmaceutical compounds.

27. A method of making a resin modified elastomer, the method comprising reacting, in the presence of a hydrosilylation catalyst,
(1) an ≡SiH functional siloxane and,
(2) a diene, diyne or ene-yne compound
(3) a resin having the formula $(R^1_3SiO_{1/2})_x(SiO_{4/2})_y (R^1SiO_{3/2})_z$ where $R^1$ is independently a monovalent hydrocarbon group having 1 to 30 carbon atoms or an unsaturated hydrocarbon group having 2 to 30 carbon atoms, and x is $\geq 1$, $y \geq 0$, $z \geq 0$ and $y+z \geq 1$;
wherein (1), (2) and (3) are dispersed in a diluent, and there is 0.1 to 100 weight parts of diluent per weight part of (1), (2) and (3).

28. The method as claimed in claim 27 wherein the ≡SiH functional siloxane contains at least two units selected from $R^3HSiO_{2/2}$, $HSiO_{3/2}$ and $R^3_2HSiO$ where $R^3$ is a monovalent hydrocarbon group.

29. The method as claimed in claim 28 wherein the ≡SiH functional siloxane contains 2 to 600 units selected from $R^3HSiO_{2/2}$, $HSiO_{3/2}$ and $R^3_2HSiO$ where $R^3$ is a monovalent hydrocarbon group.

30. The method as claimed in claim 27 wherein component (2) is a diene compound.

31. The method as claimed in claim 27 wherein component (2) is $E^1$-Y-$E^1$ or a siloxane containing aliphatic unsaturated groups with some separation between the groups, where $E^1$ are independently $CH_2$=CH— or CH≡C—; and Y is a multivalent group that is a hydrocarbon, a siloxane or some combination of these.

32. The method as claimed in claim 27 wherein component (2) is selected from 1,4-pentadiene, 1,5-hexadiene; 1,6-heptadiene; 1,7-octadiene, 1,8-nonadiene, 1,9-decadiene, 1,11-dodecadiene, 1,13-tetradecadiene, and 1,19-eicosadiene, 1,3-butadiyne, 1,5-hexadiyne (dipropargyl), and 1-hexene-5-yne.

33. The method as claimed in claim 27 wherein component (3) is a reins having the formula $(R^1_3SiO_{1/2})_x(SiO_{4/2})_y$ wherein the mole ratio of x:y has a value of from 0.5:1 to 1.5:1.

34. The method as claimed in claim 27 wherein the diluent is selected from silicones, organic oils, organic solvents or mixtures thereof.

35. The method as claimed in claim 34 wherein the diluent is a silicone.

36. The method as claimed in claim 27 wherein there is 0.05 to 50 parts of diluent per weight part of (1), (2) and (3).

37. The method as claimed in claim 27 wherein the resin is used in an amount of 0.01 to 50 mole % based on the total moles of SiH in component (1).

38. The method as claimed in claim 27 wherein component (2) is used in an amount to provide 0.7 to 1.3 part of unsaturation in (2) per part of SiH in (1).

* * * * *